(12) United States Patent
Kling et al.

(10) Patent No.: US 7,048,725 B2
(45) Date of Patent: May 23, 2006

(54) ABSORBENT STRUCTURE

(75) Inventors: Robert Kling, Skene (SE); Tomas Gandemo, Askim (SE)

(73) Assignee: SCA Hygiene Products AB (a Swedish Body Corporate), Gothenburg (SE)

( * ) Notice: Subject to any disclaimer, the term of this patent is extended or adjusted under 35 U.S.C. 154(b) by 356 days.

(21) Appl. No.: 10/147,898

(22) Filed: May 20, 2002

(65) Prior Publication Data

US 2002/0188266 A1 Dec. 12, 2002

Related U.S. Application Data

(60) Provisional application No. 60/291,645, filed on May 18, 2001.

(51) Int. Cl.
*A61F 13/15* (2006.01)

(52) U.S. Cl. ........... 604/385.01; 604/378; 604/385.101; 604/385.23; 604/385.21; 604/385.26

(58) Field of Classification Search ........... 604/385.01, 604/385.21, 385.17, 378, 385.29, 385.3, 604/385.08, 385.13, 385.23, 385.26, 385.101; 156/256, 265

See application file for complete search history.

(56) References Cited

U.S. PATENT DOCUMENTS

| | | | | |
|---|---|---|---|---|
| 2,043,325 A | * | 6/1936 | Jackson, Jr. ................ 604/375 |
| 4,195,634 A | * | 4/1980 | DiSalvo et al. ............. 604/366 |
| 4,425,130 A | * | 1/1984 | DesMarais ................... 604/389 |
| 4,726,807 A | * | 2/1988 | Young et al. .......... 604/385.26 |
| 5,134,007 A | | 7/1992 | Reising et al. |
| 5,531,729 A | * | 7/1996 | Coles et al. ................. 604/384 |
| 5,567,265 A | * | 10/1996 | Zajaczkowski ............. 156/256 |
| 5,649,920 A | * | 7/1997 | Lavon et al. ............ 604/385.3 |
| 5,853,402 A | | 12/1998 | Faulks et al. |
| 6,114,597 A | * | 9/2000 | Romare ....................... 604/378 |

FOREIGN PATENT DOCUMENTS

| | | |
|---|---|---|
| GB | 2 309 646 | 8/1997 |
| WO | WO 99/17696 | 4/1999 |
| WO | WO 99/63921 | 12/1999 |

* cited by examiner

*Primary Examiner*—Jacqueline F. Stephens
(74) *Attorney, Agent, or Firm*—Young & Thompson

(57) ABSTRACT

An absorbent product, such as a diaper or an incontinence garment, having a longitudinal and a lateral direction, includes a back sheet, being distal from the body of the wearer in use of the garment, and a top sheet, being proximal to the body of the wearer in use of the garment. The product has a front part, a rear part and a crotch part lying between the front and rear parts, and an absorbent structure between the top and back sheet extending longitudinally from the front part to the rear part. The absorbent structure includes two separate absorbent cores, wherein a first absorbent core extends longitudinally from the front to the rear part, and a second absorbent core is disposed in the front part or in the rear part.

11 Claims, 2 Drawing Sheets

ABSORBENT STRUCTURE

TECHNICAL FIELD

The invention relates to an absorbent product, such as a diaper or an incontinence garment, having a longitudinal and a lateral direction, comprising a back sheet, being distal from the body of the wearer in use of the garment, and a top sheet, being proximal to the body of the wearer in use of the garment, said product having a front part, a rear part and a crotch part lying between the front and rear parts, the product further comprising an absorbent structure, between the top and back sheet, extending longitudinally from the front part to the rear part.

BACKGROUND OF THE INVENTION

Absorbent products, such as diapers, having absorbent cores with various shapes have been known for some time. For example, the T-shaped absorbent core (U.S. Pat. No. 3,768,479) was introduced during the seventies. The T-shaped absorbent core provided an absorbent product with an absorbent structure having good fluid-storing properties, as well as it gave a good and stable fit to the wearer.

By U.S. Pat. No. 4,643,726 is an hour-glass shaped absorbent structure disclosed, which through its shape may absorb and store fluid to a greater extent than an absorbent core not being as large in size.

As mentioned, some advantages with a T-shaped and hour-glass shaped absorbent core is that the shape provides a good stability in the front part of the absorbent product. Moreover, the shape (or hour-glass shape) facilitates the absorbent structure to be correctly positioned in the longitudinal direction of the absorbent product, as it has a pre-disposed placement, due to the fitting of its shape between the legs of the wearer and the absorbent product. Further, the absorbent material of the "ears" and the front edge part of the core, not being in close proximity with the fluid waste source, i.e. urine, are used for storing fluid.

The absorbent cores are produced in a mat forming process, which usually is divided in two types: continuous and discontinuous mat forming.

In discontinuous mat forming each core is formed in a form having any desired shape. This process is advantageous due to its high flexibility with regard to the shape and surface of the core. Nevertheless, during manufacturing of an absorbent core having a T-shaped form, it has been shown that it is difficult to achieve a good absorption capacity in the "ears", as the "ears" tend to become thinner than the rest of the absorbent core. This is a result of the mat forming process, and is especially significant at high production rates, or by manufacturing of thin layers. Thus, an absorbent product manufactured by this process has a sub-optimal fluid storing capacity.

As an alternative, continuous mat forming may be used, whereby the absorption cores are cut into discrete pieces after the formation process, which pieces are placed in the absorbent product. During continuous mat forming, it is optimal to keep the longitudinal core edges straight and parallel, as one otherwise end up with the problems described above for the discontinuous mat forming. As a result of this, the products from continuous mat forming are normally absorbent products comprising cores with a rectangular surface shape. This leads to a worse fit, and frequently also to an insufficient absorption capacity in the front part of the absorbent product.

Therefore, it is an object of the invention to avoid the drawbacks of the prior art and provide an absorbent product having an enhanced fluid storing capacity in the front part of the absorbent core.

Furthermore, it is an object of the invention to provide an absorbent product which provides a good fit and stability to the wearer, and which can be produced at a high production rate.

SUMMARY OF THE INVENTION

These and other objects of the invention are accomplished by an absorbent product, such as a diaper or an incontinence garment, having a longitudinal and a lateral direction, comprising a back sheet, being distal from the body of the wearer in use of the garment, and a top sheet, being proximal to the body of the wearer in use of the garment, said product having a front part, a rear part and a crotch part lying between the front and rear parts, the product further comprising an absorbent structure, between the top and back sheet, extending longitudinally from the front part to the rear part, characterised in that the absorbent structure comprises at least two separate absorbent cores, whereby at least one first absorbent core extends longitudinally from the front to the rear part, and at least one second absorbent core is diposed in the front part or in the rear part.

In this way, an absorbent structure is provided, in which the separate parts may be manufactured independently from each other, thereby making it possible to vary the thickness, size and absorption capacity of the separate cores. Accordingly, a great flexibility is introduced, whereby size, shape and capacity of a specific absorbent product may be adjusted for its purpose.

Moreover, another aspect of the invention is an absorbent product, whereby the first absorbent core is equipped with a wicking layer, which specifically may be designed for spreading fluid towards the front part of the first absorbent core.

This makes it possible to use the first absorbent core, being in close proximity with the fluid source, for spreading the fluid towards the front and into the second absorbent core, whereby the second absorbent core mainly functions as a storage for the fluid waste. Preferably, the first absorbent core overlaps the second core (distance m is shorter than distance $b_2$ (FIG. 1)), in order for the fluid to be transferred from the first to the second core.

Furthermore, as yet another aspect of the invention, a method for manufacturing a T-shaped absorbent product is provided, comprising the steps of:

(a) providing a backing sheet or a top sheet forming a continuously moving web;

(b) providing an absorbent core;

(c) applying the absorbent core of step (b) on the sheet by a first applicator device;

(d) providing another absorbent core;

(e) applying the absorbent core of step (d) on the absorbent core of step (b) and/or on the sheet forming the continuously moving web by a second applicator device, whereby at least one of the absorbent cores extends longitudinally from the front to the rear part, and at least one of the cores is disposed in the front part or in the rear part;

(f) applying a top or backing sheet on the absorbent structure on the continuously moving web, whereby the product at this stage comprises one top and one backing sheet in addition to the absorbent cores;

(g) nipping the product of step (f) between rollers.

In this way, the two cores are manufactured independently from each other, thereby avoiding the drawbacks of the prior art, such as the uneven distribution of the absorbent material, and are thereafter put together, to form the T-shaped absorbent structure. Accordingly, the different size, thickness, shape, and content of the two different absorbent cores can be greatly varied. Moreover, the absorbent cores may be provided in three different ways: continuous mat-forming, discontinuous mat-forming, and as a prefabricated core, preferably being stored as a roll goods or as festooned blocks.

DETAILED DESCRIPTION OF THE INVENTION

By a "T-shaped" absorbent structure is meant a structure, which, by its shape, essentially defines a "T", whereby the cross-leg of the T is positioned in the front part or in the rear part of the diaper, and the longitudinal leg of the T extends from the front to the rear part of the diaper.

By an "absorbent core" is hereby meant a single body of material having absorbent properties.

By "essentially parallel longitudinal edges" of the core is meant that the core edges are essentially parallel with each other.

Figure 1:
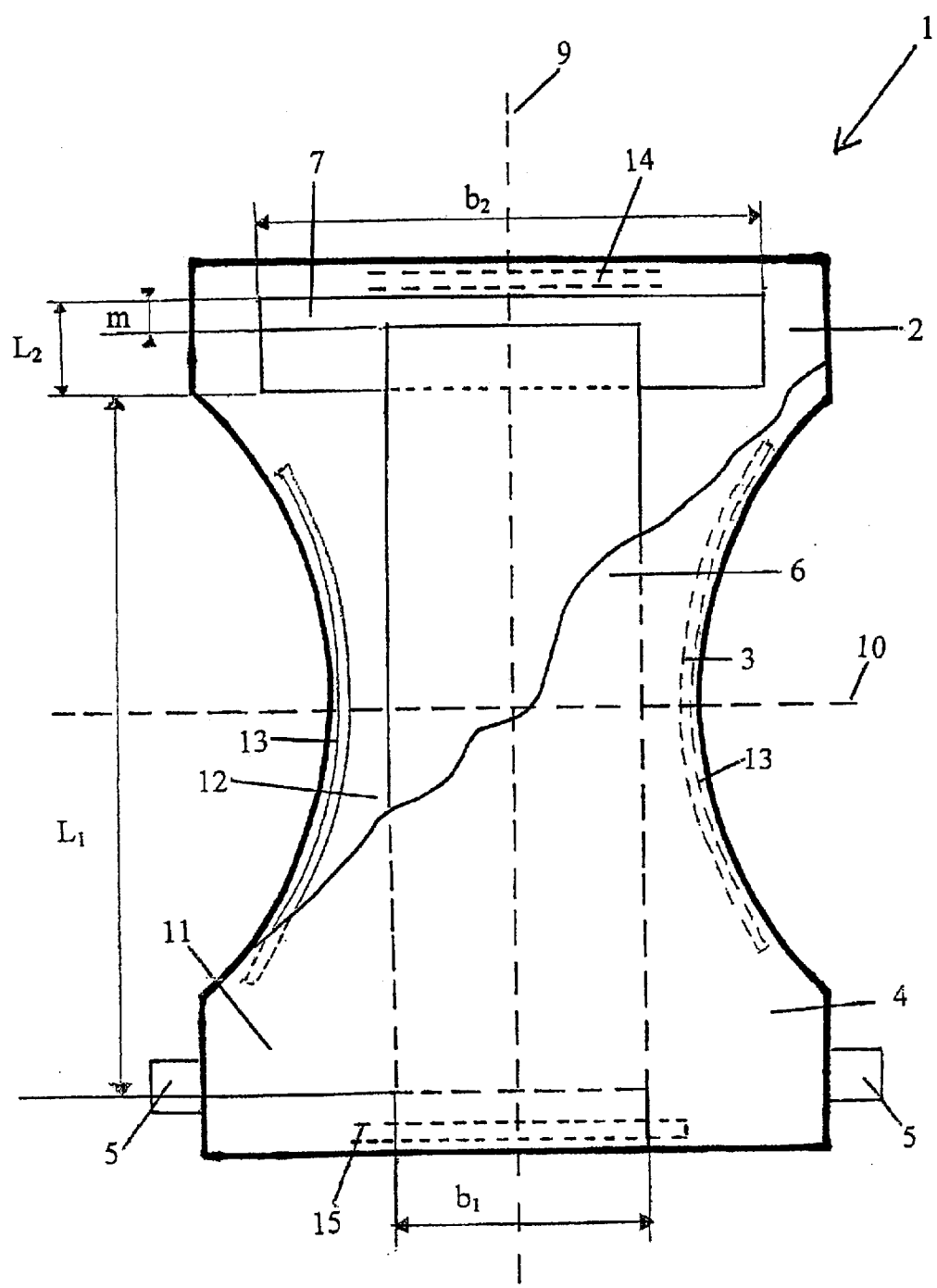
FIG. 1 is a schematic view of an absorbent product according to the invention.

FIG. 1 discloses a diaper 1. As is conventional in this field of the art, the diaper comprises an absorbent structure 6, 7, being enclosed between a liquid-permeable top sheet 11 and a liquid-impermeable backing sheet 12, these sheets being fastened to each other in portions thereof reaching beyond the absorbent body. The diaper has a front part 2, a rear part 4 and an intermediate crotch part 3, whereby the longitudinal direction of the diaper extends from the rear to the front edge thereof. The top sheet and the backing sheet constitute a casing for the absorbent structure 6, 7, and the side portions of the front 2 and rear part 4 of the diaper 1 are laterally projecting from the front and rear parts in relation to the extension of the casing in the crotch part 3 of the diaper.

The absorbent structure comprises two separate bodies: the first absorbent core 6 and the second absorbent core 7. The first absorbent core has the function of a regular absorbent core being in proximity with the waste fluid source, i.e. to absorb and spread fluid waste, i.e. urine. The second absorbent core mainly has the function of storage of liquid waste. The individual sizes of the first and second absorbent core may be greatly varied. The first absorbent core has the length $l_1$ of 200–600 mm and the width $b_1$ of 50–250 mm. The second absorbent core has the length $l_2$ of 50–150 mm and the width $b_2$ of 80–250 mm. Preferably, the width $b_2$ is equal to or greater than the width $b_1$. The thickness of the first and second absorbent core may also be greatly varied, whereby the first absorbent core has the thickness of 2–7 mm, and the second absorbent core has the thickness of 2–7 mm. Accordingly, during the mat-forming process, the number of layers used may vary between the different cores. Moreover, the shapes of the different cores may be varied. They need not have rectangular shapes, but any other shape, being possible to manufacture, and which gives the desired properties, may also be used, such as an hour-glass shaped absorbent core. These possible variations make it possible to provide an absorbent structure having the desired absorbing properties and shape, thereby providing a great flexibility in the manufacturing, which can be used to optimise the absorbent structure for the purpose of fluid storage, wearer fit and fluid spreading, to mention but a few parameters. For example, the second absorbent core may have essentially non-parallel longitudinal edges, thereby providing a good fit to the wearer.

The absorbent cores 6, 7 is preferably formed of cellulose fibres but also other natural materials, such as cotton fibres or peat can be used. Alternatively, absorbent synthetic fibres or a mixture of natural and synthetic fibres may be used. The absorbent cores can also comprise a super-absorbent, i.e. a polymer having the capacity to absorb liquid to an amount several times larger than its own weight. At least one of the absorbent cores comprises at least 25% (w/w) of SAP. The absorbent cores can also contain form stabilising and/or liquid dispersing components and also bonding agents for holding together short fibres and particles to a continuous unit. Furthermore, the absorbent cores can contain more than one layer of absorbent material. Moreover, the different cores may be formed of different material, thereby providing cores having different absorbent properties. In one preferred aspect of the invention, an enhanced absorption capacity is desired in the front part of the diaper. For instance, this can be accomplished by producing a second absorbent core having a greater content of super-absorbent polymers than the first core.

The liquid-permeable top sheet is preferably made of a material showing properties like dryness and softness at use of the absorbent product, as this sheet lies against the body of the wearer. It is desired, that the sheet has a soft and textile-like surface, which remains dry also at repeated wettings. The top sheet may for example be composed of nonwoven material with a soft and smooth surface, such as for example a spunbond made of polypropylene fibres. In order to keep the surface closest to the skin of the wearer dry, a hydrophobic nonwoven-material may be used, which has holes, so that openings are formed in the material, which openings are greater than the cavities between the fibres of the material. In this way, fluid may be lead down through the holed openings in the top sheet to the underlying absorption core. Other examples of material in the top sheet may for example be holed plastic films, such as for example a holed polyethylene film. The top sheet may be connected to the underlying backing sheet and to the absorption core by, for example, glue or through some kind of thermal bonding.

The liquid-impermeable backing sheet consists of a flexible material, preferably a thin plastic film of PE (polyethylene), PP (polypropylene), a polyester, or some other kind of suitable material, such as a hydrophobic nonwoven-layer or a laminate of a thin film and a nonwoven material. These types of laminates are often used in order to achieve a soft and a textile-like surface of the backing sheet. In order to accomplish an airier and comfortable product it is also possible to use breathable backing sheets, which prevents fluid from coming out of the absorbent product, but that allows moisture to be ventilated. These breathable backing sheets may be composed of single material layers, or of laminates of, for example, blown or moulded polyethylene films, which have been laminated with, for example, a nonwoven layer of spunbond or of spunbond-meltblown-spunbond (SMS).

The absorption body is typically built up by one or more layers of cellulose fibres, for example cellulose fluff pulp. Other materials, which may be used, are for example absorbing nonwoven material, foam material, synthetic fibre materials or peat. In addition to cellulose fibres or other absorbing materials, the absorbent body may also comprise superabsorbent material, so called SAP (super absorbent polymers), that is material in the form of fibres, particles, granula, film or the like, which material has the ability to absorb fluid corresponding to several times the weight of the superabsorbent material. The superabsorbent material binds the fluid and forms a fluid-containing gel. Moreover, the absorbent body may comprise binders, form-stabilising components or the like. Additional layers improving the properties may also be used, such as various types of fluid-spreading material layers or inserts, so called waddings. The absorbent body may be chemically or physically treated in order to change the absorption properties. For instance, it is possible to provide an absorbent layer with compressed regions and/or being compressed in the entire layer(s) in order to control the fluid flow in the absorbent body. It is also possible to enclose the absorbent layer(s) in an envelope of for example tissue material.

Typically, the absorbent body has in its longitudinal direction an outstretched form, and may for example be essentially rectangular, T-shaped or hourglass-shaped. In a T-shaped absorbent body, the lateral part is at use adapted for being positioned towards the front part of the absorbent product, so that it at use is in the area around the belly of the user. An hourglass-shaped absorbent body is wider in the front and rear parts than in the crotch part, in order to provide an efficient fluid absorption simultaneously as the design facilitates the product to form and to close around the user, thereby giving a better fit around the legs.

Those parts on each side of the central part, which extend outside the absorbent body and between the rear and front side portion are preferably equipped with one or more elastic organs 13, at least in the part of the absorbent product which at use forms the crotch part. The elastic organs function as leg elastics, and have as their purpose to prevent fluid and faeces to leak out through the longitudinal edges, and thereby form outer fluid barriers. The elastic organs may be composed of one or several elastic threads, which in stretched state are applied between the backing sheet and the top sheet, or between the backing sheet and a separate sheet outside the top sheet in the lateral direction. The separate sheet may be composed of a strip, which extends along the absorbent body and the longitudinal edges. Alternatively, the elastics may be applied between the sheets in an un-stretched state, whereby instead both sheets are gathered or wrinkled at the application. It is also possible to apply the elastics on the outside of the backing sheet or on the inside of the top sheet.

In order to further prevent fluid or faeces to leak out, the absorbent product on the side that is facing the wearer may also be equipped with inner fluid barriers, which are attached in connection to the longitudinal edges inside the outer barriers. Preferably, the inner barriers are made of an essentially liquid-impermeable material, such as for example a hydrophobic nonwoven or a plastic film, and are formed as a longitudinal path with a first edge being connected to the absorbent product and a second free edge, which is adapted for being in close contact with the user at use of the absorbent product. The second edge is equipped with one or more elastic elements, preferably an elastic thread, which in contracted state contracts the free edge, whereby an upstanding barrier is formed. The inner barrier may be designed as a strip of a single sheet, wherein the free edge is turned down in order to enclose the elastic element to prevent direct contact of the elastic thread to the user. Alternatively, the barrier may be formed of two combined layers, whereby the elastic thread is attached to the edge of the free end between the two layers. In this case, the inner layer of the barrier may be composed of an elongation of the top sheet and the outer layer of an essentially liquid-impermeable material, or the inner and outer layers of the barrier may be composed of one single material strip, which is folded around the elastic thread.

The rear and/or front parts of the product may also be equipped with a so called waist elastics 14, 15, which is composed of elastic organs applied along the front and/or rear end edges in order to give the product a soft and flexible enclosure around the waist of the user. Suitably, the elastic organs are attached between the backing sheet and the top sheet with glue or through welding, such as ultra-sonic welding. The elastic organs may be composed of one or more elastic threads, which in a stretched state are applied between the sheets, and thereby form the waist elastics. Alternatively, the elastics may be applied between the sheets in an unstretched state, whereby both sheets instead are gathered or wrinkled at application. Another typical variant of the elastics, which is suitable, is elastic foam material composed of a thin strip of for example polyurethane foam, which like the elastic threads can be applied between the two sheets. Of course, it is also possible to position the elastic organs for the waist elastics on the outside of the backing sheet or on the inside of the top sheet.

The absorbent product may comprise a fastening system. This fastening system may be of any kind, which is suitable for the product, such as a hook and loop system, or a tape. The product may also be a pant diaper, thereby not having a fastening system for attaching opposing side portions to each other.

Preferably, the first absorbent core is placed with an overlap on the second absorbent core. It is fully possible, though, to put second absorbent core on the first absorbent core. Moreover, it also fully possible to use two "second" absorbent cores, whereby one is put under and the other is put over the first absorbent core, i.e. the first absorbent core is sandwiched between the other cores.

In one embodiment according to the invention, the first absorbent core is positioned in a way making it overlapping the second absorbent core. This means that the distance m in FIG. 1 is shorter than the distance $1_2$ of the second absorbent core, in this case. Preferably, the distance m is within the interval ranging from 0 to 150 mm, thus being equal to or smaller than the distance $1_2$.

When using two separate cores as in the invention, and when fluid is to flow from one core to the other, it is important to achieve a good contact between the two cores. Furthermore, it is important to use capillary forces in the absorbent material, and in an optional wicking layer, for moving fluid in the desired direction. As one of the cores overlaps the other, the joint will tend to be somewhat compressed, resulting in smaller capillaries, which in turn causes fluid to be drawn in the direction towards the smaller capillaries. This effect can also be used if sandwiched cores are used, as discussed above.

In yet another embodiment, the first absorbent core is equipped with a wicking layer, which wicking layer has the purpose to spread fluid towards the front part of the absorbent structure. Thereby, liquid is spread to the second absorbent core, which is used for liquid storage. Moreover, the wicking layer does not necessarily need to cover the whole first absorbent core, but should preferably cover at least the part of the first absorbent core being in the front part of the casing, more preferably the part being in the front and crotch parts of the casing, and most preferably the entire first absorbent core.

The wicking layer is of a moisture permeable material, preferably tissue paper or a hydrophilic non-woven, and functions to disperse the fluid, i.e. urine, passing through the liquid permeable top sheet, preferably in a direction towards the front part of the diaper. The wicking layer comprises small capillaries directing the fluid towards smaller capillaries, due to capillary forces.

Figure 2:
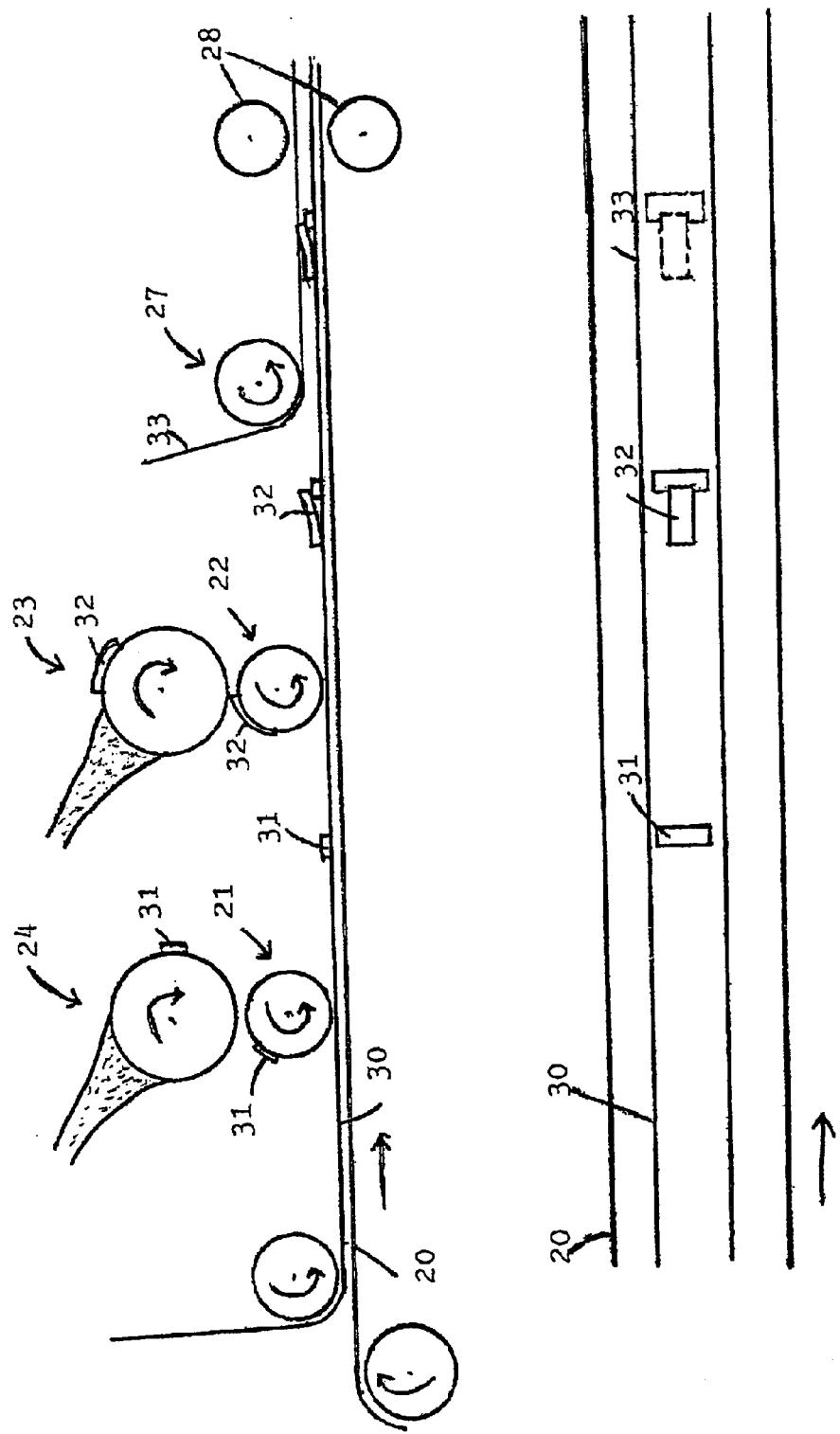
FIG. 2 is a schematic illustration of the manufacturing process according to the invention.

FIG. 2 illustrates the manufacturing of an absorbent product according to the invention. As can be seen there an absorbent product is manufactured on a continuously moving belt 20. Two applicator devices 21, 22 can be seen. Over the applicator devices are mat-forming devices 23, 24 positioned. In this embodiment, the second absorbent core 31 is formed by the mat-forming device in connection with the first applicator device 21, and a backing sheet 30 forming a continuously moving web is applied by the applicator device. The second core 31 is placed on the continuously moving web so that the edge of the second core that is to be closest to the front of the absorbent product points in the direction of movement of the continuously moving belt 20. The first absorbent core 32 is formed by the mat-forming device being connected to the second applicator device 22, and is placed on the second absorbent core 31 in order to form a T-shaped absorbent structure. Thereafter, a top sheet is applied on the T-shaped absorbent structure 33, the T-shaped absorbent structure thereby being packaged in a casing. Next, the casing is nipped between rollers, in order to create a good contact between the cores and also to compress the cores, which creates smaller capillaries, thereby creating better fluid spreading properties in the absorbent material. Thereafter, the casing is sealed, and cut to thereby constitute a finished absorbent product. This finished absorbent product is subsequently packaged in an outer package.

The first and the second absorbent core may be manufactured by discontinuous mat-forming (as in FIG. 2), or by continuous mat-forming. Furthermore, the absorbent cores may be provided as prefabricated cores, preferably being stored on a roll. Any regular diaper manufacturing machine may be used for the mat-forming process.

In order for the absorbent cores to be steady positioned between the top and back sheets, the area of the top and back sheets surrounding the cores may contain glue, thereby preventing the cores from sliding.

Furthermore, the thickness of the absorbent cores in an overlapping relation, may before wetting preferably be less than 5 mm, measured with an applied pressure of 0.1 N/cm$^2$.

Still further, the first core may have a substantially rectangular shape, and two opposing cut outs in the crotch part, in order to improve the fit in the crotch part.

Moreover, other shapes of the absorbent structure, differing from the T-shape, are possible within the scope of the invention. For example, one or more, preferably rectangular shaped, absorbent cores, may be combined, in order to provide an absorbent structure having the advantages discussed above. For example, it is possible to provide an absorbent structure having an improved absorption capacity in the rear or front part of the diaper, or an absorbent structure having improved absorption capacity in both the rear and the front part of the diaper.

Still further, the second absorbent core may be positioned in the rear part of the absorbent product.

Further, the T-shaped absorbent structure of the invention may also be used for other absorbent products than diapers. For example, incontinence garments or sanitary napkins may be mentioned.

What is claimed is:

1. An absorbent product selected from the group consisting of a diaper and an incontinence garment, having a longitudinal direction and a lateral direction, comprising a liquid-impermeable back sheet, which in use is distal from the body of a wearer, and a liquid-permeable top sheet, which in use is proximal to the body of the wearer; said product having a front part, a rear part and a crotch part lying between the front and rear parts; the product further comprising an absorbent structure between the top sheet and the back sheet, extending longitudinally from the front part to the rear part; the absorbent structure comprising at least two separate absorbent cores, whereby at least one first absorbent core extends longitudinally from the front part to the rear part and has a substantially rectangular shape, and at least one second absorbent core is disposed only in the front part or the rear part; the first absorbent core being in fluid communication with the second absorbent core; and the width of the second absorbent core being greater than the largest width of the first absorbent core, such that the first and second absorbent cores form a T-shaped absorbent structure.

2. The absorbent product according to claim 1, wherein the length of the first absorbent core is in the interval of 200–600 mm, the width of the first absorbent core is in the interval of 50–250 mm, the length of the second absorbent core is in the interval of 50–150 mm, and the width of the second absorbent core is in the interval of 80–250 mm.

3. The absorbent product according to claim 1, wherein at least one of the absorbent cores comprises at least 25% (w/w) of super absorbent polymers.

4. The absorbent product according to claim 1, wherein the distance from a front edge of the first absorbent core to an edge of the second absorbent core being closest to a front edge of the absorbent product, is shorter than the length of the second absorbent core.

5. The absorbent product according to claim 4, wherein the distance ranges between 0 and 150 mm.

6. The absorbent product according to claim 4, wherein the second absorbent core is on top of the first absorbent core, and faces the top sheet.

7. The absorbent product according to claim 1, wherein the first and second absorbent cores have a thickness before wetting in an overlapping relation, which is less than 5 mm, measured with an applied pressure of 0.1 N/cm$^2$.

8. The absorbent product according to claim 1, wherein the first absorbent core comprises a wicking layer for spreading fluid towards the front part of the first absorbent core.

9. The absorbent product according to claim 1, wherein the absorbent product has two opposing cut outs in the crotch part.

10. The absorbent product according to claim 1, wherein the first absorbent core has substantially parallel longitudinal edges.

11. The absorbent product according to claim 1, wherein the second absorbent core has a width which is greater than its length.

* * * * *